(12) United States Patent
O'Halloran et al.

(10) Patent No.: US 9,328,244 B2
(45) Date of Patent: May 3, 2016

(54) SURFACE-TREATED CALCIUM CARBONATE, METHODS FOR MAKING THE SAME, AND COMPOSITIONS INCLUDING THE SAME

(71) Applicant: Sensient Colors LLC, St. Louis, MO (US)

(72) Inventors: David O'Halloran, Mill Town, NJ (US); Kelly Chen, Fair Lawn, NJ (US)

(73) Assignee: Sensient Colors LLC, St. Louis, MO (US)

( * ) Notice: Subject to any disclaimer, the term of this patent is extended or adjusted under 35 U.S.C. 154(b) by 0 days.

(21) Appl. No.: 14/613,543

(22) Filed: Feb. 4, 2015

(65) Prior Publication Data

US 2015/0218381 A1    Aug. 6, 2015

Related U.S. Application Data

(60) Provisional application No. 61/936,160, filed on Feb. 5, 2014.

(51) Int. Cl.
| | |
|---|---|
| *A61Q 1/02* | (2006.01) |
| *C09C 1/02* | (2006.01) |
| *A61Q 1/06* | (2006.01) |
| *A61K 8/58* | (2006.01) |
| *A61K 8/19* | (2006.01) |
| *A61Q 1/12* | (2006.01) |
| *A61K 8/02* | (2006.01) |

(52) U.S. Cl.
CPC ............... *C09C 1/021* (2013.01); *A61K 8/0241* (2013.01); *A61K 8/19* (2013.01); *A61K 8/585* (2013.01); *A61Q 1/02* (2013.01); *A61Q 1/06* (2013.01); *A61Q 1/12* (2013.01); *C09C 1/02* (2013.01); *A61K 2800/623* (2013.01); *A61K 2800/651* (2013.01)

(58) Field of Classification Search
USPC .................. 556/457; 510/122, 119, 181, 186
See application file for complete search history.

(56) References Cited

U.S. PATENT DOCUMENTS

| | | | |
|---|---|---|---|
| 7,964,178 B2 | 6/2011 | Gutkowski et al. | |
| 8,846,087 B2 | 9/2014 | Young | |
| 2004/0092639 A1 | 5/2004 | Kasahara et al. | |
| 2007/0071821 A1 | 3/2007 | Young | |
| 2007/0253989 A1 | 11/2007 | Abe et al. | |
| 2009/0185984 A1 | 7/2009 | Gutkowski et al. | |
| 2009/0318594 A1* | 12/2009 | Grothe et al. ................. | 524/148 |
| 2014/0377313 A1 | 12/2014 | Young | |

FOREIGN PATENT DOCUMENTS

WO    WO2011082019 A1    7/2011

OTHER PUBLICATIONS

Morel; European Polymer Journal; 2012, 48, 919-929.*
International Search Report and Written Opinion for International Application No. PCT/US2015/014394 dated May 26, 2015, 13 pages.
Morel et al., Surface modification of calcium carbonate nanofillers by fluoro- and alkyl-alkoxysilane: Consequences on the morphology, thermal stability and gas barrier properties of polyvinylidene flouride nanocomposites, European Polymer Journal 48 (2012) 919-929.

* cited by examiner

*Primary Examiner* — Sudhakar Katakam
*Assistant Examiner* — Pancham Bakshi
(74) *Attorney, Agent, or Firm* — Whyte Hirschboeck Dudek S.C.

(57) ABSTRACT

In an embodiment, the invention provides a surface treated calcium carbonate and method for making the same. In embodiments, the calcium carbonate is surface treated with a hydrophobic compound, such as a trialkoxyalkylsilane (i.e., triethoxycaprylylsilane), fluoro high purity ammonium $C_{6-16}$ perfluoroalkyl phosphate, or dimethicone trimethylsiloxysilane.

In another embodiment, the invention provides a personal care product comprising the surface treated calcium carbonate. In embodiments, the personal care product is a darker skin tone makeup.

11 Claims, No Drawings

US 9,328,244 B2

SURFACE-TREATED CALCIUM CARBONATE, METHODS FOR MAKING THE SAME, AND COMPOSITIONS INCLUDING THE SAME

FIELD OF THE INVENTION

The present invention relates to surface treated calcium carbonate, specifically calcium carbonate surface treated with a trialkoxyalkylsilane, and products comprising the same.

BACKGROUND OF THE INVENTION

Colorants, which include pigments and dyes, are used in a variety of personal care products. Titanium dioxide is commonly used as a pigment in liquid foundations, sunscreens and personal care products. However, titanium oxide has been prohibited in certain applications, such as aerosol application, due to health concerns.

Calcium carbonate is another pigment commonly used in personal care products. Currently, calcium carbonate is not prohibited in personal care products due to health concern. Calcium carbonate is therefore viewed as a potential replacement for titanium dioxide. However, due to calcium carbonate's hydrophilic nature, calcium carbonate is not easily incorporated into many personal care products such as liquid foundation formulations and aerosol personal care products, which include water. Calcium carbonate swells in the presence of water, resulting in clumping and agglomeration.

In order to render calcium carbonate useful in a wide-range of personal care products, it is desirable to modify calcium carbonate with a hydrophobic material. Current hydrophobic compounds which are used to modify pigments include lauroyl lysine, natural flower waxes and glutamate cysteine arginine. These compounds, however, only provide a physical surface treatment to pigment particles and do not bind to the calcium carbonate. Other surface treatments, such as hydrogenated lecithin, will bind to pigment particles, but require water to apply the treatment.

It is desirable to use calcium carbonate as a replacement for titanium dioxide in personal care products. It is further desirable to surface treat calcium carbonate with a hydrophobic compound and develop a method for surface treating calcium carbonate with a hydrophobic compound which does not require significant amounts of water.

SUMMARY OF THE INVENTION

In an embodiment, the invention provides a surface treated calcium carbonate and method for making the same. In embodiments, the calcium carbonate is surface treated with a hydrophobic compound, such as a trialkoxyalkylsilane (i.e., triethoxycaprylylsilane), fluoro high purity ammonium $C_{6-16}$ perfluoroalkyl phosphate, or dimethicone trimethylsiloxysilane.

In another embodiment, the invention provides a personal care product comprising the surface treated calcium carbonate. In embodiments, the personal care product is a darker skin tone makeup.

DETAILED DESCRIPTION OF THE PREFERRED EMBODIMENT

Definitions

Unless stated to the contrary, implicit from the context, or customary in the art, all parts and percents are based on weight, and all test methods are current as of the filing date of this disclosure. For purposes of United States patent practice, the contents of any referenced patent, patent application or publication are incorporated by reference, in their entirety (or its equivalent US version is so incorporated by reference), especially with respect to the disclosure of definitions (to the extent not inconsistent with any definitions specifically provided in this disclosure) and general knowledge in the art.

"Comprising", "including", "having" and like terms are not intended to exclude the presence of any additional component, step or procedure, whether or not the same is specifically disclosed. In order to avoid any doubt, all processes claimed through use of the term "comprising" may include one or more additional steps, pieces of equipment or component parts, and/or materials unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or," unless stated otherwise, refers to the listed members individually as well as in any combination.

As used herein, "surface treating" generally refers to contacting calcium carbonate with a hydrophobic compound such as a trialkoxyalkylsilane (i.e., triethoxycaprylylsilane), fluoro high purity ammonium $C_{6-16}$ perfluoroalkyl phosphate, or dimethicone trimethylsiloxysilane. Similarly, the term "surface treatment" refers to an effective amount of hydrophobic compound that, when contacted with calcium carbonate, improves at least one of the following properties: hydrophobicity (i.e., water resistance), adherence to the surface of skin and/or hair, skin feel (i.e., softness/smoothness to touch), and combinations thereof.

As used herein, the term "hydrophobicity," when referring to the property of calcium carbonate, whether surface treated or not, and/or a personal care product composition including calcium carbonate, generally indicates the ability of the calcium carbonate and/or personal care product to repel or absorb water. Unmodified calcium carbonate is generally hydrophilic and tends to absorb water, whereas calcium carbonate which has been surface treated with a hydrophobic compound tends to repel more water than untreated calcium carbonate. Hydrophobicity can be determined, for example, by placing drops of water onto pressed calcium carbonate and/or the personal care product and measuring the time it takes the water to disappear into the calcium carbonate/product. The longer time taken, the more hydrophobic the calcium carbonate/product. Less hydrophobic (i.e., hydrophilic) calcium carbonates/compositions tend to absorb droplets of water quickly, in less than about 20 seconds. More hydrophobic calcium carbonates/compositions tend to repel droplets of water for more than about 30 seconds.

As used herein, "adherence to the surface of the skin and/or hair," when referring to a property of calcium carbonate, whether surface treated or not, and/or a personal care product composition containing calcium carbonate, generally indicates the ability of the calcium carbonate and/or personal care product to resist transfer from skin and/or hair to another medium. Adherence to the surface of the skin and/or hair can be measured, for example, by applying the calcium carbonate and/or personal care product to skin and/or hair and then pressing a piece of tissue paper onto the skin or hair. Most calcium carbonate (colorant) is removed from the skin/hair onto the tissue paper when the adherence of the calcium carbonate and/or personal care product composition to the surface of the skin and/or hair is low. The amount of calcium carbonate and/or personal care product transferred to the tissue paper can, for example, be visually inspected or measured by weight.

Surface Treated Calcium Carbonate

In one embodiment, the invention is a surface treated calcium carbonate, and specifically calcium carbonate surface treated with a hydrophobic compound. The surface treated calcium carbonate may comprise one or more embodiments described herein.

Surface treated calcium carbonate may be used as a colorant in personal care product compositions. It was surprisingly discovered that calcium carbonate surface treated with a hydrophobic compound improves at least one of the hydrophobicity (i.e., water resistance), adherence to the surface of skin and/or hair, and skin feel (i.e., softness/smoothness to touch) of a personal care product compositions containing the surface treated calcium carbonate. These properties may be improved compared to a personal care product composition containing calcium carbonate not having the surface treatment.

Suitable hydrophobic compounds useful in surface treating calcium carbonate include, but are not limited to, trialkoxyalkylsilanes (i.e., triethoxycaprylylsilane), fluoro high purity ammonium $C_{6-16}$ perfluoroalkyl phosphates, dimethicone trimethylsiloxysilane, and a combination of isopropyl titanium triisostearate and bis-hydroxyethylpropyle dimethicone/PEG-2 soyamine/isophorone diisocyanate (IPDI) copolymer. Although each of the preferred hydrophobic treatments may be used to surface treat calcium carbonate, trialkoxyalkylsilanes, and specifically triethoxycaprylylsilane, and ADT are preferred because of their lower cost and superior results.

In embodiments, the hydrophobic compound used to surface treat calcium carbonate is a trialkoxyalkylsilane, more preferably triethoxycaprylylsilane.

Surface Treatment Process

Typically, surface treatment processes using trialkoxyalkylsilane (e.g., triethoxycaprylylsilane) and ADT use water to wet the surface of colorant particles and create a catalyst for the hydrogen bonding of the hydrophobic compound to the colorant. Once the colorant is sufficiently wet, the surface treating compound is added to the colorant to form a surface treating composition. Typically, the surface treating composition comprises 1-3 wt % water, based on the total weight of the composition. The surface treating composition is blended and chopped with high heat to promote bonding of the hydrophobic compound and colorant and drive over any solvent. The colorant is then dried in a curing oven for several hours.

However, because calcium carbonate is hydrophilic, water levels of 0.25-0.50 wt % or greater cause the particles to swell, as well as clumping and agglomeration. Typical surface treatment processes are therefore not suitable for calcium carbonate and often result in uneven, rough calcium carbonate particles.

In an embodiment, the present invention provides a process for making surface treated calcium carbonate. In one embodiment, the process includes (1) wetting calcium carbonate particles slowly with water so that the water is evenly blended into the calcium carbonate particles to form calcium carbonate particles having a smooth and homogeneously wetted surface, and (2) quickly blending the surface treating material into the water and calcium carbonate mixture to form a surface treated calcium carbonate particulate material.

In other embodiments, the process includes wetting the calcium carbonate particles simultaneously with the addition of the surface treatment to form the wet surface treated calcium carbonate particulate material.

In an embodiment, the calcium carbonate may be surface treated (i.e., wetted and blended with the surface treating material) using processes and equipment known in the art, such as by spraying or atomizing the surface treating material onto the surface of the calcium carbonate. The calcium carbonate particles may be agitated by air or other mechanical means during application of the water and/or surface treating material.

After the wetted calcium carbonate and surface treatment are blended together, the wet surface treated calcium carbonate particulate material is dried in an oven to drive off or remove most or essentially all of the free water. The resulting dried surface treated calcium carbonate particles are suitable for use in a variety of personal care products, including makeup formulations, sunscreens, and hair products.

In an embodiment, the wet surface treated calcium carbonate particulate material comprises greater than or equal to 90 wt %, or greater than or equal to 95 wt %, or greater than or equal to 97 wt % calcium carbonate, based on the total weight of the wet surface treated calcium carbonate particulate material. The amount of water used in the process described herein is from greater than 0.00 wt % to less than 1 wt %, or from greater than 0.00 wt % to less than or equal to 0.75 wt %, or from greater than 0 wt % to less than or equal to 0.50 wt %, or from greater than 0.00 wt % to less than or equal to 0.25 wt %, based on the total weight of the wet surface treated calcium carbonate particulate material. The amount of hydrophobic surface treatment (i.e., triethoxycaprylylsilane and/or ADT) used in the process described herein is from greater than 0 wt % to less than or equal to 10 wt %, or from greater than 0 wt % to less than or equal to 5 wt %, or from greater than 0 wt % to less than or equal to 3 wt %, based on the total weight of the wet surface treated calcium carbonate particulate material.

In a preferred embodiment, the wet surface treated calcium carbonate particulate material comprises 97.75 wt % calcium carbonate, 0.25 wt % water and 2.0 wt % triethoxycaprylylsilane.

In embodiments, additional materials, such as soy amines, may be added to the wet surface treated calcium carbonate particulate material. Such additional materials may improve the adhesion of the surface treated calcium carbonate particles to skin.

The surface treatment disclosed herein imparts a smooth velvety feel to the calcium carbonate. In water-in-silicone and water-in-oil emulsions, the surface treated calcium carbonate reduces the viscosity of the final formulation, improving spreadability of the emulsion during application to the skin. IN pressed powder, the surface treated calcium carbonate improves adhesion of the powdered cosmetic to the skin. The surface treated calcium carbonate also provides advantages in that it improves the cohesiveness of the pressed powder, allowing less binder to be used in the formulation and/or lower compression forces to be used during formation of the pressed powder.

Applications

The surface treated calcium carbonate as described herein can be used in multiple applications for cosmetic use, such as personal care products including, but not limited to, cosmetics and hair care products. Cosmetic products can include, but are not limited to, mascaras, pressed powder makeups (e.g., eye shadows, cheek rouge, facial powders), liquid makeups (e.g., eye shadows, foundations, cheek rouge, blushes, lip liners, eye liners, nail enamel), lipsticks and other cosmetics made using silicones, or combinations thereof. Other personal care products may include, but are not limited to, lotions, creams, gels, toothpastes, and combinations thereof. The surface treated calcium carbonate as described herein may also be used in paints, inks, leather and other surface treatments in other industries (e.g., automobile industry, print industry).

Applicants originally developed the surface treated calcium carbonate for aerosol applications, such as spray hair color (i.e., "hair chalk") to avoid the safety concerns of inhalation of titanium dioxide or zinc oxide. However, it was discovered that using untreated calcium carbonate in place of titanium dioxide/zinc oxide in aerosol applications resulted in compositions which clumped and clogged the spraying mechanisms when applying the personal care product. Due to the presence of water in the personal care product formulation, the calcium carbonate particles swelled and clumped, resulting in uneven distribution of the product and, in some cases, clogging of the spray nozzle.

Surprisingly, it was discovered that surface treating the calcium carbonate with a hydrophobic compound, such as, for example, a trialkoxyalkylsilane triethoxycaprylylsilane) or ADT prevented the calcium carbonate particles from swelling, resulting in a personal care product formulation which did not clump or clog the spraying mechanisms. Further, the personal care product had improved hydrophobicity (i.e., water resistance), adherence to the surface of skin and/or hair, and skin feel (i.e., softness/smoothness to touch) compared to a personal care products containing calcium carbonate not having the surface treatment.

The surface treated calcium carbonate is also ideal for personal care products having deeper shades at a standard percent pigment of 5-15%. However, the surface treated calcium carbonate does not give the opacity or coverage of traditional zinc oxide and titanium oxide, so higher levels of surface treated calcium carbonate may be required to achieve that effect.

The surface treated calcium carbonate may also be used to replace micro-fine titanium dioxide used in darker skin toned makeup. Standard titanium dioxide creates a white or ashen appearance on darker skin tones. Using micro-fine titanium dioxide in darker skin tone makeup solved the white/ashen appearance problem. However, micro-fine titanium dioxide is more costly than standard titanium dioxide or calcium carbonate. The surface treated calcium carbonate is less expensive than micro-fine titanium dioxide and, as it was surprisingly discovered, can easily replace the micro-fine titanium traditionally used in darker skin toned makeup.

The surface treated calcium carbonate particles can also be combined with a variety of other components to form one or more of the products listed above and herein. Additional components may include, but are not limited to, at least one of other colorants, water soluble sunscreens (such as Eusolex 232); oil soluble sunscreens (such as octyl methoxycinnamate); and organic sunscreens (such as camphor derivatives, cinnamates, salicylates, benzophenones, triazines, PABA derivatives, diphenylacrylate derivatives, and dibenzoylmethane derivatives); antioxidants (such as BHT); chelating agents (such as disodium EDTA); emulsion stabilizers (such as carbomer); preservatives (such as methyl paraben); fragrances (such as pinene); flavoring agents (such as sorbitol); humectants (such as glycerine); waterproofing agents (such as PVP/Eicosene copolymer); water soluble film-formers (such as hydroxypropyl methylcellulose); oil-soluble film formers (such as hydrogenated C-9 resin); moisturizing agents, such as cholesterol; cationic polymers (such as Polyquatemium 10); anionic polymers (such as xanthan gum); pigment wetting agents, such as Arlacel™ P100 (polyhydroxystearic acid) or Emerest™ 2452 (polyglyceryl-3 diisostearate); vitamins (such as tocopherol) or combinations thereof.

Examples of other components that can be combined with the surface treated calcium carbonate particles to form one or more of the products listed herein include, but are not limited to, fats and oils, waxes, surfactants, oxidation inhibitors, UV absorbers, vitamins, hormones, squalenes, liquid paraffins, fatty acids, bees wax, myristyl myristate and other esters, acetone, toluene, butyl acetate, acetic ester and other solvents; antioxidants, antiseptic agents, polyhydric alcohols, perfumes and combinations thereof.

Exemplary Personal Care Product Compositions

In embodiments, the personal care product composition is an emulsion, such as a foundation or concealer, comprising from 2 wt % to 20 wt % of a surface treated calcium carbonate, based on the total weight of the composition. An emulsion may be very liquid (low viscosity), very thick (high viscosity) or a cream. In embodiments, the emulsion is a hot poured product.

A specific exemplary composition for a long lasting foundation is provided in Table 1, below.

TABLE 1

Long Lasting Foundation Composition

| Component | Weight % |
|---|---|
| Phase A | |
| Silamer (phenyl trimethicone, cetyl PEG/PPG-10/1 dimethicone, polyglyceryl-2-isostearate, hexyl laurate) | 5.00-15.00 |
| DC 2502 cosmetic fluid (cetyl dimethicone) | 1.00-3.00 |
| Synthetic beeswax | 0.25-1.00 |
| Hydrogenated castor oil | 0.10-1.00 |
| Cetiol A (hexyl laurate) | 0.70-3.70 |
| Phase B | |
| DC 245 (cyclopentasiloxane) | 5.00-15.00 |
| Phase C | |
| Water | 40.00-55.00 |
| Sodium chloride | 0.40-1.00 |
| Propylene glycol | 2.00-4.00 |
| Microcare PM3 (phenoxyethanol, methyl/ethyl and propylparaben) | 0.20-1.00 |
| Phase D | |
| Submica M (mica) | 2.50-7.50 |
| Phase E | |
| Yellow LC 182 HLC (hydrogenated lecithin) | 0.60-1.50 |
| Red LC 381 HLC (hydrogenated lecithin) | 0.15-1.50 |
| Black LC 989 HLC (hydrogenated lecithin) | 0.05-1.00 |
| Surface treated calcium carbonate | 5.00-10.00 |

In embodiments, the personal care product composition is an anhydrous suspension comprising from 2 wt % to 20 wt % of a surface treated calcium carbonate, based on the total weight of the composition.

In embodiments, the personal care product is a loose or pressed powder, and specifically a loose or pressed powder for darker skin tones or for translucent powders. Such powders are used to add coverage and evening of skin tone or to add brightness to dull skin. A personal care product formulation for use as a loose or pressed powder comprises from 5 to 95 wt % surface treated calcium carbonate, based on the total weight of the composition, depending on the final desired effect and skin tone.

An exemplary composition for a loose powder comprising the surface treated calcium carbonate is provided in Table 2, below.

TABLE 2

Loose Powder Composition

| Component | Weight % |
|---|---|
| Phase A | |
| Surface treated calcium carbonate | 10.0-25.0 |
| Yellow LC 182 NFW Rose CF (*Rosa centifolia* flower wax, cera alba) | 2.0-10.0 |
| Red LC 381 NFW Rose CF (*Rosa centifolia* flower wax, cera alba) | 2.0-10.0 |
| Black LC 989 NFW Rose CF (*Rosa centifolia* flower wax, cera alba) | 2.0-10.0 |
| Phase B | |
| Submica FL (mica) | 15.0-30.0 |
| Natpure Hollowbead (calcium aluminum borosilicate, silica) | 15.0-30.0 |
| Covafluid FS (sodium stearyl fumarate) | 0.05-1.0 |
| Phase C | |
| Covapearl Fire Red 333 (CI 77491, mica) | 1.00-15.0 |

An exemplary composition for a powdery foundation comprising the surface treated calcium carbonate is provided in Table 3, below.

TABLE 3

Powdery Foundation Composition

| Component | Weight % |
|---|---|
| Phase A | |
| Surface treated calcium carbonate | 20.0-30.0 |
| Talc HIP (talc, ammonium $C_6$-$C_{16}$ perfluoroalkylethyl phosphate) | 5.0-10.0 |
| Covabead LH 170 (methylmethacrylate crosspolymer) | 2.0-5.0 |
| Red LC 388 FHP (ammonium $C_6$-$C_{16}$ perfluoroalkylethyl phosphate) | 0.01-1.00 |
| Yellow LC 188 FHP (ammonium $C_6$-$C_{16}$ perfluoroalkylethyl phosphate) | 0.05-3.00 |
| Black LC 988 FHP (ammonium $C_6$-$C_{16}$ perfluoroalkylethyl phosphate) | 0.01-1.00 |
| Phase B | |
| Squatol S (hydrogenated polyisobutene) | 45.00-55.00 |
| Phase C | |
| Submica M (mica) | 5.00-10.00 |

In embodiments, the personal care product is a lipstick or lip gloss, particularly for deeper shades where higher color pigment loads are required, although the surface treated calcium carbonate can also be used in lipsticks and lip glosses with a lighter pink shade as well.

An exemplary composition for a lipstick comprising the surface treated calcium carbonate is provided in Table 4, below.

TABLE 4

Lipstick Composition

| Component | Weight % |
|---|---|
| Phase A | |
| *Macadamia ternifolia* seed oil | 8.00-22.00 |
| Macamat wax (*macadamia ternifolia* seed oil, ozokerite, hydroxystearic acid, stearic acid, palmitic acid) | 18.00-28.00 |
| Castor oil | 15.00-25.00 |
| Covasterol (glyceryl isostearate, isostearyl alcohol, *brassica campestris* (rapeseed) sterols, *butyrospermum parkii* butter, candelilla cera) | 8.00-13.00 |
| Phase B | |
| Covapate Unired LC 3779 (with *Ricinus communis* seed oil) | 0.30-1.00 |
| Covapate Uniblack LC 9789 (with *Ricinus communis* seed oil) | 0.05-0.06 |
| Covapate Unibrown LC 8781 (with *Ricinus communis* seed oil) | 1.00-3.00 |
| Phase C | |
| Surface treated calcium carbonate | 2.50-8.00 |
| Mica NBSB (mica, *butyrospemum parkii* butter, cera alba, candelilla cera) | 10.00-15.00 |
| Covapearl sparkling silver 937 HCL (mica and hydrogenated lecithin) | 0.20-1.50 |

In embodiments, the personal care product is a nail polish, specifically a nail polish having a frosted or shear look. A surface treated calcium carbonate as described herein may be used to replace more costly pearlized pigments and/or talc in nail polish compositions.

In embodiments, the personal care product is an eye shadow or eye liner, specifically a frosted eye shadow or eye liner. The surface treated calcium carbonate may be used to replace talc and titanium dioxide in eye shadows and eye liners.

Although the invention is described herein with reference to specific embodiments, it will be appreciated by those of ordinary skill in the art that various modifications and changes can be made without departing from the scope of the present disclosure as set forth in the claims below. Accordingly, the specification is to be regarded in an illustrative rather than a restrictive sense, and all such modifications are intended to be included within the scope of the present disclosure. Any benefits, advantages, or solutions to problems that are described herein with regard to specific embodiments are not intended to be construed as a critical, required or essential feature or element of any or all of the claims. For the purposes of United States patent practice, the contents of any referenced patent, patent application or publication are incorporated by reference in their entirety.

The invention claimed is:

1. A composition comprising:
   calcium carbonate particles;
   water; and
   a hydrophobic compound selected from the group consisting of a trialkoxyalkylsilane and a combination of isopropyl titanium triisostearate and bis-hydroxyethylpropyl dimethicone/PEG-2 soyamine/isophorone diisocyanate (IPDI) copolymer (ADT);
   wherein the calcium carbonate particles are coated with the hydrophobic compound.

2. The composition of claim 1, wherein the hydrophobic compound is a trialkoxyalkylsilane.

3. The composition of claim 1, wherein the hydrophobic compound is triethoxycarpylylsilane.

4. The composition of claim 1, wherein the hydrophobic compound is a combination of isopropyl titanium triisostearate and bis-hydroxyethylpropyl dimethicone/PEG-2 soyamine/isophorone diisocyanate (IPDI) copolymer (ADT).

5. The composition of claim 1, comprising:
   greater than or equal to 90 wt % calcium carbonate,
   from greater than 0 wt % to less than 1 wt % water; and
   from greater than 0 wt % to less than or equal to 10 wt % of trialkoxyalkylsilane.

6. The composition of claim 1 being void of titanium dioxide.

7. A composition consisting of surface coated calcium carbonate particles, wherein the surface coating comprises a hydrophobic compound and water, wherein the hydrophobic compound is selected from the group consisting of a trialkoxyalkylsilane and a combination of isopropyl titanium triisostearate and bis-hydroxyethylpropyl dimethicone/PEG-2 soyamine/isophorone diisocyanate (IPDI) copolymer (ADT).

8. The composition of claim 7, consisting of:
   ≥90 wt % calcium carbonate particles;
   ≥0 to <1 wt % water; and
   ≥0 to ≤10 wt % of the hydrophobic compound.

9. The composition of claim 1, wherein the hydrophobic compound is dimethicone trimethylsiloxysilane.

10. The composition of claim 1, wherein the hydrophobic compound is selected from the group consisting of trialkoxyalkylsilanes, a combination of isopropyl titanium triisostearate and bis-hydroxyethylpropyl dimethicone/PEG-2 soyamine/isophorone diisocyanate (IPDI) copolymer (ADT), dimethicone trimethylsiloxysilane, and combinations thereof.

11. The composition of claim 1, wherein the hydrophobic compound is selected from the group consisting of dimethicone trimethylsiloxysilane and a combination of isopropyl titanium triisostearate and bis-hydroxyethylpropyl dimethicone/PEG-2 soyamine/isophorone diisocyanate (IPDI) copolymer (ADT).

* * * * *